(12) United States Patent
Yan et al.

(10) Patent No.: US 10,147,228 B2
(45) Date of Patent: Dec. 4, 2018

(54) INTEGRATED METHOD FOR THREE-DIMENSIONAL VISUALIZATION RECONSTRUCTION OF THE FASCICULAR STRUCTURE INSIDE HUMAN PERIPHERAL NERVES

(71) Applicants: THE FIRST AFFILIATED HOSPITAL OF SUN YAT-SEN UNIVERSITY, Guangzhou, Guangdong (CN); SCHOOL OF DATA AND COMPUTER SCIENCE OF SUN YAT-SEN UNIVERSITY, Guangzhou, Guangdong (CN); NATIONAL SUPERCOMPUTER CENTRE IN GUANGZHOU OF SUN YAT-SEN UNIVERSITY, Guangzhou, Guangdong (CN)

(72) Inventors: Liwei Yan, Guangdong (CN); Shuang Zhu, Guangdong (CN); Xiaolin Liu, Guangdong (CN); Jian Qi, Guangdong (CN); Qingtang Zhu, Guangdong (CN); Yao Lu, Guangdong (CN); Yongze Guo, Guangdong (CN); Sha Yu, Guangdong (CN); Yutong Lu, Guangdong (CN); Xi Zhang, Guangdong (CN); Yunfei Du, Guangdong (CN); Tao Lin, Guangdong (CN)

(73) Assignees: THE FIRST AFFILIATED HOSPITAL OF SUN YAT-SEN UNIVERSITY, Guangzhou (CN); SCHOOL OF DATA AND COMPUTER SCIENCES OF SUN YAT-SEN UNIVERSITY, Guangzhou (CN); NATIONAL SUPERCOMPUTER CENTRE IN GUANGZHOU OF SUN YAT-SEN UNIVERSITY, Guangzhou (CN)

(*) Notice: Subject to any disclaimer, the term of this patent is extended or adjusted under 35 U.S.C. 154(b) by 56 days.

(21) Appl. No.: 15/623,363

(22) Filed: Jun. 14, 2017

(65) Prior Publication Data

US 2018/0018816 A1    Jan. 18, 2018

Related U.S. Application Data

(63) Continuation of application No. PCT/CN2016/089992, filed on Jul. 14, 2016.

(51) Int. Cl.
    *G06K 9/00* (2006.01)
    *G06T 17/00* (2006.01)
    (Continued)

(52) U.S. Cl.
    CPC ............... *G06T 17/00* (2013.01); *G01N 1/30* (2013.01); *G06T 7/10* (2017.01); *G06T 15/04* (2013.01);
    (Continued)

(58) Field of Classification Search
    CPC ........... G06T 17/00; G06T 7/10; G06T 15/04; G01N 1/30
    See application file for complete search history.

(56) References Cited

U.S. PATENT DOCUMENTS

2005/0069525 A1*  3/2005  Mikael .................... A61L 27/20
                                                                424/93.7

OTHER PUBLICATIONS

Qi, Jian et al., Preliminary Research of 3D Reconstruction of Short-Segment Common Peroneal Nerve Functional Fascicles, Chinese Journal of Reparative and Reconstructive Surgery, Sep. 2008, pp. 1031-1035, vol. 22, No. 9, China Academic Journal Electronic Publishing House.

(Continued)

*Primary Examiner* — Duy M Dang (57) ABSTRACT

The present invention relates to fields of clinical application of nerve defect repair and the medical three-dimensional (Continued)

(3D) printing technology, and provides an integrated visualization method for three-dimensional (3D) reconstruction of internal structure of human peripheral nerves. The method comprises the following steps: obtaining human peripheral nerves, preparing nerve specimens ex vivo by staining with an iodine preparation in combination with a freeze-drying method; scanning the pretreated peripheral nerves using Micro CT to acquire lossless two-dimensional images, and performing binarization processing to the two-dimensional images, then conducting image segmentation based on textural features to acquire images of nerve fascicles; finally, reconstructing the segmented images into a visualization model by using a supercomputer.

10 Claims, 9 Drawing Sheets

(51) Int. Cl.
*G06T 7/10* (2017.01)
*G01N 1/30* (2006.01)
*G06T 15/04* (2011.01)

(52) U.S. Cl.
CPC . *G01N 2001/302* (2013.01); *G01N 2001/305* (2013.01); *G06T 2207/10081* (2013.01); *G06T 2207/30004* (2013.01); *G06T 2210/41* (2013.01); *G06T 2215/16* (2013.01)

(56) References Cited

OTHER PUBLICATIONS

International Search Report of PCT Patent Application No. PCT/CN2016/089992 dated Mar. 29, 2017.

* cited by examiner

INTEGRATED METHOD FOR THREE-DIMENSIONAL VISUALIZATION RECONSTRUCTION OF THE FASCICULAR STRUCTURE INSIDE HUMAN PERIPHERAL NERVES

CROSS REFERENCE TO RELATED APPLICATIONS

This application is a continuation application of PCT Application No. PCT/CN2016/089992 filed on Jul. 14, 2016, the entire contents of which are incorporated herein by reference.

FIELD OF THE INVENTION

The present invention relates to fields of clinical application of nerve defect repair and the medical three-dimensional (3D) printing technology, and in particular provides an integrated visualization method for three-dimensional reconstruction of internal fascicular structure of human peripheral nerves.

BACKGROUND OF THE INVENTION

The primary function of peripheral nerves is to connect the central nervous system with target organs, and also play a role of conveying information. Peripheral nerves contain internal nerve fascicles, the internal nerve fascicles of peripheral nerves can be divided into sensory fascicles, motion fascicles and mixed fascicles. The primary functions of these nerve fascicles are to afferent and efferent information. It is well known that the most optimal repair methods in clinical is to achieve anastomosis between functional fascicles once an injury or defect of human peripheral nerves occurs. However, since the anatomical structure of human peripheral nerve fascicles is quite complicated, a precondition for clinicians is understanding of the anatomical structure law and morphology of fascicular type of human peripheral nerves in order to achieve a goal of anastomosis between functional fascicles. A visualization model of internal fascicular structure obtained for reconstruction of human peripheral nerve three-dimensional structure is expected to provide an effective method for improving the functional recovery after peripheral nerve defect.

On the other hand, three-dimensional reconstruction of human peripheral nerve fascicles also holds a more far-reaching significance, with the development of modern bio-manufacturing technology, biomimetic manufacture of many tissues and organs has already been achieved. But it is very difficult to achieve the biomimetic manufacture of peripheral nerves, the reasons are chiefly as follows: ① the internal structure of nerves is complicated and fine, the required precision cannot be achieved using the existing bio-manufacturing methods; ② each piece of, and even each segment of nerve fascicle has its own corresponding biological functions, which have not been fully understood for the present. The visualization model of three-dimensional reconstruction of peripheral nerve fascicles will solve the above problems being faced during bio-manufacturing of peripheral nerve biomaterials, namely to achieve a standard of precision medicine.

In terms of three-dimensional reconstruction of peripheral nerve fascicles, many scholars have done a lot of research, for example, understanding of three-dimensional anatomical structure of human nerve fascicles by Sunderland has undergone the following process: it was initially regarded as frequently crossing on the same plane, whereas at present it is observed that vascular network is formed at its proximal end, and at its distal end fascicles are frequently mixed or divided into several small fascicles. Jian Qi et al. reconstructed a three-dimensional structure of the median nerve using the histological section method on peripheral nerves, at the same time they also found the complexity in configuration of nerve fascicles. However, all these methods of reconstructing three-dimensional anatomical structure of peripheral nerve fascicles have their own disadvantages, such as inadequate precision in acquiring two-dimensional structure, bad matching in the course of reconstruction, image distortion and involvement of abundant anthropic factors. Therefore, it is quite necessary to seek a simple and effective technical method which is capable of capturing two-dimensional images with high resolution and simultaneously achieving a successive matching at the three-dimensional level.

With the development of modern technology, computed tomography (CT) and magnetic resonance imaging (MRI) have become the major imaging means for three-dimensional reconstruction. But because the internal structure of peripheral nerves are relative fine, such scanning precision cannot be achieved using the existing MRI. Therefore, it is urgent currently to find a method to construct a visualization model for internal fascicles structure of human peripheral nerves and to implement a three-dimensional reconstruction of human peripheral nerves.

SUMMARY OF THE INVENTION

In order to solve the above problems, and construct a visualization model for internal fascicular structure of human peripheral nerves, the present invention performs a scan on the pretreated specimens of human peripheral nerves using Micro CT to acquire the most excellent, biomimetic and lossless two-dimensional images, followed by automatic segmentation on nerve fascicles, and quickly executes the three-dimensional reconstruction using powerful computer processing systems.

The present invention provides a constructing method for visualization models of human peripheral nerve fascicles, comprising the following steps of:

obtaining human peripheral nerves, staining with an iodine preparation and combination with freeze-drying;

scanning the stained peripheral nerves by using Micro CT to acquire two-dimensional lossless images, and performing binarization processing of the two-dimensional images to acquire segmented images of nerve fascicles;

reconstructing the segmented images into visualization models.

The present invention also provides a method for three-dimensional reconstruction of human peripheral nerves, comprising the following steps of:

obtaining human peripheral nerves, staining with an iodine preparation in combination with freeze-drying;

scanning the stained peripheral nerves by using Micro CT to acquire two-dimensional lossless images, and performing binarization processing of the two-dimensional images to acquire segmented images of nerve fascicles;

reconstructing the segmented images into visualization models.

The present invention has the following beneficial effects:
1. The invention performs a scan on the pretreated specimens of human peripheral nerves using Micro CT, enabling the accuracy to meet the requirements of reconstructing nerve fascicles. The technology for pretreating specimens can also be used for other soft tissues to achieve two-dimensional lossless images with high resolution; 2. Three-dimensional visualization models of peripheral nerve fascicles are able to provide the stereoscopic anatomical atlas required for interfascicular nerve anastomosis in clinical practice; 3. The invention will lay the technical foundation for visualization processing of massive medical pictures by using a supercomputer; 4. The invention will create templates for bio-manufactured neurobiological materials to achieve a goal of precise repair; 5. Different from the prior art in which nerve specimens require section processing, the method provided in the present invention has no any damage to specimens, which can be used in living bodies; 6. In the prior art, the acquired images by using microscope photography have some disadvantages, such as image distortion, requirement of processing by human intervention, and involvement of abundant anthropic factors, whereas the method provided in the present invention is able to acquire lossless two-dimensional images with high resolution, and in the meanwhile achieves a successive matching at the three-dimensional level, it is easy to operate and the results are more accurate.

BRIEF DESCRIPTION OF DRAWINGS

FIGS. 2A to 2D show Micro CT scanned images of peripheral nerve structures acquired after different pretreatment ways, wherein

FIGS. 3A to 3C show Micro CT images of the specimens after staining by adding an iodine preparation followed by freeze-drying to remove moisture, wherein FIGS. 4A-4C show generally morphological changes in the course of pretreatment on peripheral nerve specimens, wherein

FIGS. 5A-5D show automatic segmentation process of peripheral nerve fascicles, wherein

FIGS. 6A-6D show views after three-dimensional visualization reconstruction of peripheral nerve fascicles, wherein

DETAILED DESCRIPTION OF THE EMBODIMENTS

In order to make the technical problems to be solved, technical solutions and advantages of the present invention clearer, the content of the invention will now be described in more detail with reference to figures and embodiments below. It should be understood that the specific embodiments described herein are only for purpose of illustration and not to be construed as limitations of the present invention.

Figure 1:
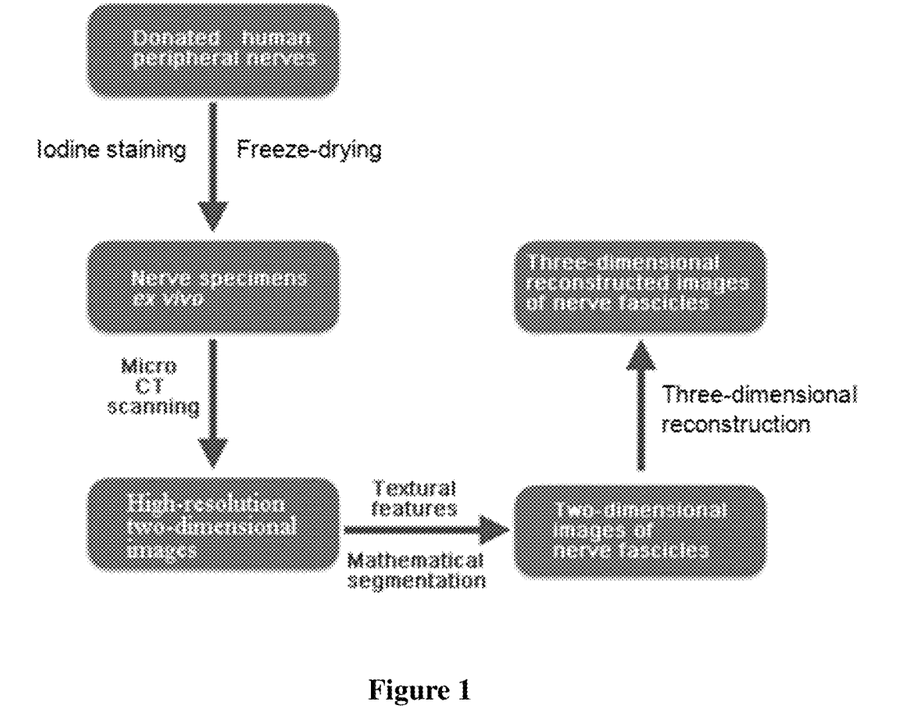
FIG. 1 shows a flowchart of the preparation method for visualization models of internal fascicular type of human peripheral nerves according to an embodiment of the present invention.

The embodiment of the present invention provides a method for internal fascicular structure visualization of human peripheral nerves used in the course of three-dimensional reconstruction of human peripheral nerves, refer to FIG. 1 which shows the main process flows of the method in the present invention. As shown in FIG. 1, the method comprises the following steps:

A constructing method for visualization models of human peripheral nerve fascicles, comprising the following steps of:

obtaining human peripheral nerves, staining with an iodine preparation in combination with freeze-drying;

scanning the stained peripheral nerves by using Micro CT to acquire lossless two-dimensional images, and performing binarization processing of the two-dimensional images to acquire segmented images of nerve fascicles;

reconstructing the segmented images into visualization models.

In the prior art, it is general to perform a scan immediately after staining, and the obtained images in this way have a poor quality in performance. After freeze-drying to remove moisture, the contrast ratio of the scanned images is increased.

Specifically, the method of the present invention comprises the following specific steps:

(1) performing a pretreatment on the fresh isolated human peripheral nerves, making them satisfy the conditions of two-dimensional lossless images with high resolution by Micro CT scanning;

(2) obtaining the optimal parameters for scanning the pretreated specimens of peripheral nerves to achieve two-dimensional images with high resolution, by adjusting scanning parameters of Micro CT;

(3) conducting image segmentation based on diverse grayscale difference and internal structure features of nerve images acquired by scanning, and developing a mathematical algorithm suitable for segmentation on peripheral nerve fascicles using integrative classic mathematical formulas;

(4) with regard to the massive segmented pictures of nerve fascicles, performing three-dimensional reconstruction of visualization models of peripheral nerve fascicles by using supercomputers with powerful computing and processing capacities.

Figure 2A:
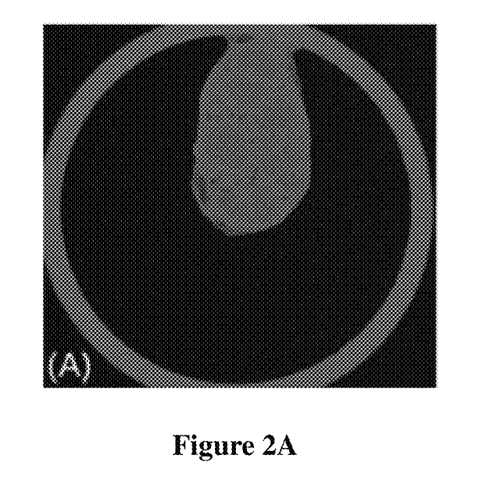
FIG. 2A shows the image of a fresh nerve without any treatment.
Figure 2B:
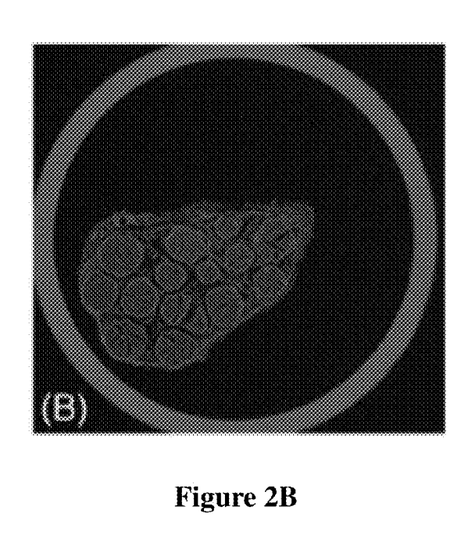
FIG. 2B shows the image of the fresh nerve after treatment with a freeze-drying method.
Figure 2C:
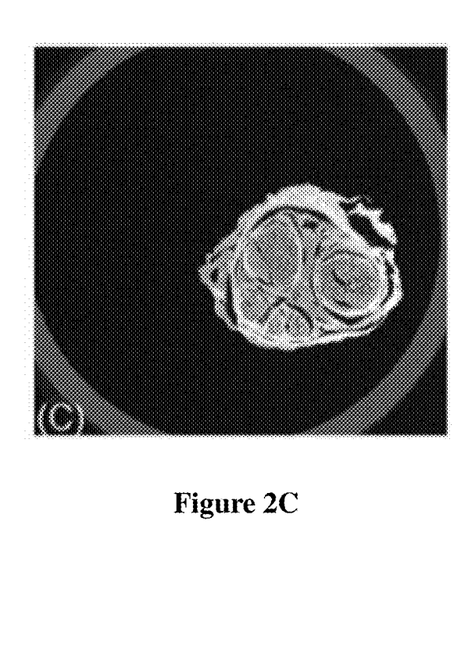
FIG. 2C shows the image of a nerve specimen after treatment of just adding an iodine preparation.
Figure 2D:
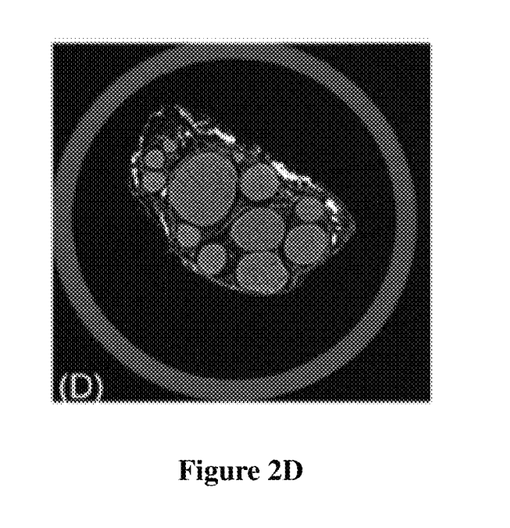
FIG. 2D shows the image of a nerve specimens after adding an iodine preparation followed by freeze-drying.

FIGS. 2A to 2D show different images of peripheral nerve structures acquired by Micro CT scanning after undergoing different pretreatment ways, wherein FIG. 2A refers to the image of fresh nerve, without any treatment (FN); FIG. 2B refers to the image of fresh nerve after treatment with a freeze-drying method (FDN); FIG. 2C refers to the image just adding an iodine preparation (IN); FIG. 2D refers to the image after adding an iodine preparation followed by freeze-drying (IFDN).

Preferably, human peripheral nerves are fixed with a fixing agent before staining with the iodine preparation, and preferably, the fixing agent is 3.5%-4.5% paraformaldehyde solution, or 9%-11% glutaraldehyde solution.

According to the specific embodiment, the iodine preparation is 40%-50% iodine solution, namely the aqueous solution of iodine, which can be self-prepared or purchased from the market.

Preferably, the specimens of human peripheral nerves are wrapped with tinfoil and placed in liquid nitrogen for quick-freezing before the freeze-drying process, in order to prevent specimen morphology from being changed and in turn to avoid affecting the subsequent scanning imaging treatment.

Specifically, the specimens of human peripheral nerves are wrapped with tinfoil, placed in liquid nitrogen and frozen for 0.5-2 minutes.

Figure 3A:
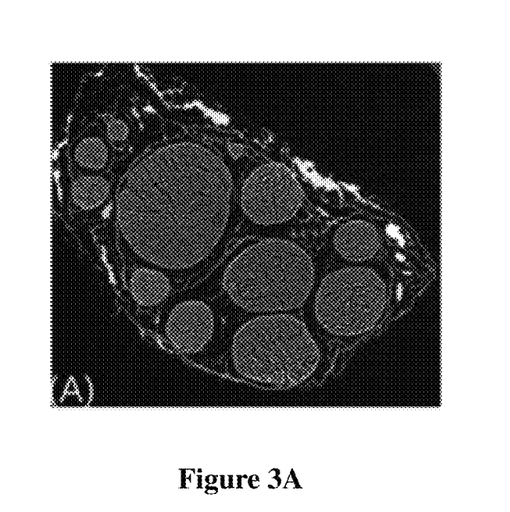
FIG. 3A shows the two-dimensional planar image of peripheral nerve.
Figure 3B:
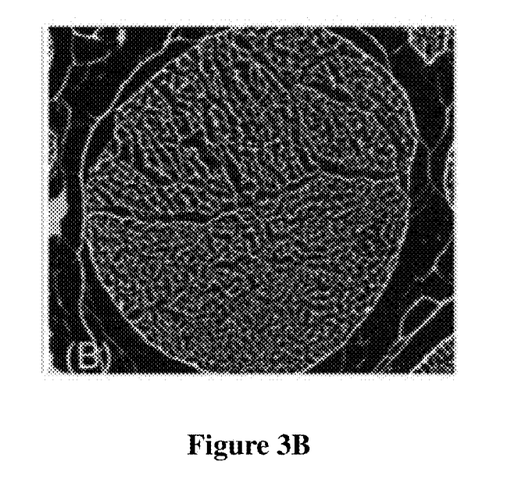
FIG. 3B shows the image of nerve fascicle.
Figure 3C:
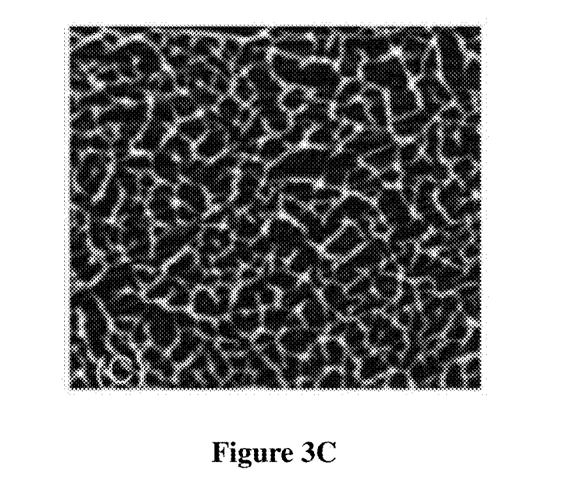
FIG. 3C shows the image of endoneurium.

FIGS. 3A-3C show Micro CT images after the specimens being freeze-drying to remove moisture before which the specimens have been stained by adding the iodine preparation, wherein FIG. 3A refers to the two-dimensional planar image of peripheral nerve; FIG. 3B refers to the image of nerve fascicle; FIG. 3C refers to the image of endoneurium.

Specifically, the specimens of peripheral nerves are placed in the freeze-dryer at a temperature of −80° C. to remove moisture during freeze-drying. The removal of moisture is extremely important for the subsequent scanning. If the moisture is removed insufficiently, the scanning effect will decrease significantly.

Figure 4A:
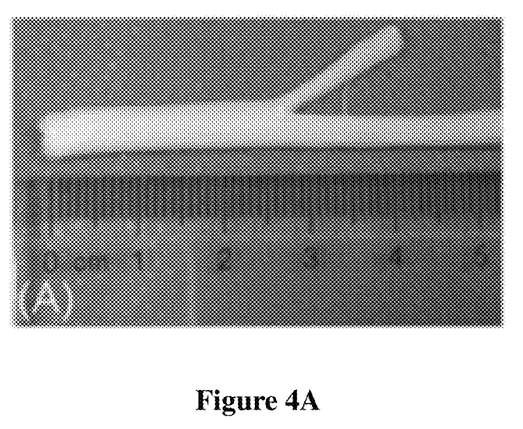
FIG. 4A shows the fresh nerve.
Figure 4B:
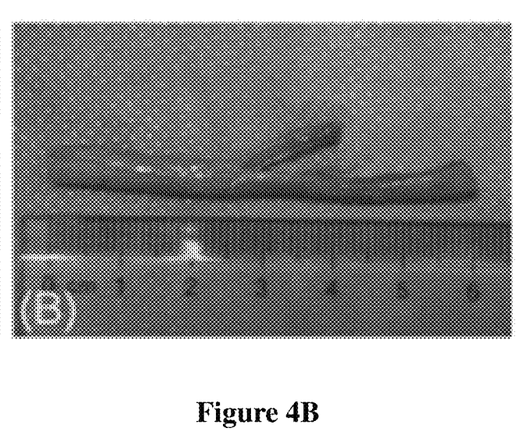
FIG. 4B shows the nerve stained with the iodine preparation.
Figure 4C:
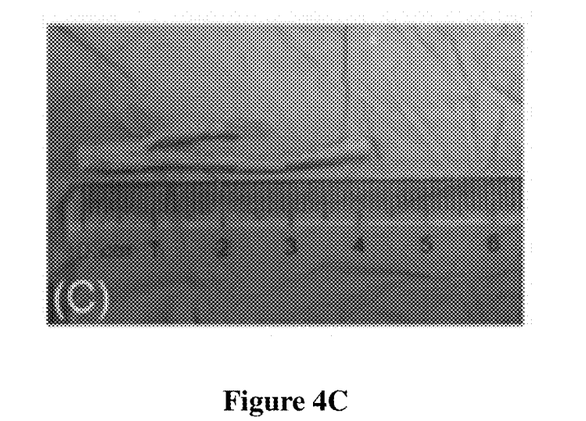
FIG. 4C shows the nerve stained with the iodine preparation and followed by freeze-drying.

FIGS. 4A-4C show the generally morphological changes of the peripheral nerve in the course of pretreatment, wherein FIG. 4A refers to the fresh nerve (FN); FIG. 4B refers to the nerve stained with the iodine preparation (IN); FIG. 4C refers to the nerve stained with the iodine preparation and followed by freeze-drying (IFDN).

In the present invention, the reconstruction of three-dimensional anatomical structure of peripheral nerve fascicles is realized by Micro CT. The advantages of Micro CT imaging is the resolution of imaging is pretty high, and the ultrastructure of tissues, namely within 10 μm, can be distinguished from the acquired images, which can even be used to analyze the mechanical properties of tissue scaffolds, thereby helping to improve the design and manufacture of ultrastructure of the scaffolds. According to reports from the existing literature, the disadvantages reside in the fact that the main principle of imaging is relied on attenuation ratio after X-rays penetrate different tissues, as a result, soft tissues with the same density cannot be differentiated. In theory, such properties are more suitable for reconstruction of hard tissues, accordingly it is quite convenient for Micro CT to be used in bone tissue imaging, whereas difficult in soft tissues, especially peripheral nerves, due to the almost same density in soft tissues and lack of contrast, resulting in a failure of imaging. In order to achieve an imaging goal in soft tissues using Micro CT, addition of contrast agent is the main solution, such as injection of contrast agents into knee joints and lungs, which have already been realized.

So far there has been no report on three-dimensional reconstruction of soft tissues using Micro CT, while in the present invention, staining with an iodine preparation is adopted to increase the contrast ratio when Micro CT scans peripheral nerve structures, achieving better effects.

On the other hand, in order to acquire peripheral nerve images with high resolution by using Micro CT, it is not enough to just use a method of adding staining agents. Inventors of the present invention also find that moisture has a huge impact on transmission of X-rays after analyzing the conditions of Micro CT scanning and making improvements to them, therefore, in order to acquire images with high resolution, we utilize the best method for keeping morphology, namely freeze-drying method, to remove the moisture of nerve specimens, and simultaneously in combination with an adjustment to Micro CT parameters. In the experiments, lossless two-dimensional images are first acquired by integrating the two techniques, from which the entire internal structures of peripheral nerves can be observed.

Specifically, in terms of parameter adjustment, the diameter of visual field, namely the inner diameter of scanning tube, is set to 9 mm, in the meanwhile the voxel size is set to 3 μm. If the voxel value is set too high, the scanning accuracy will be decreased, while the voxel value is less than 3 μm, which will result in overloaded operation of the scanner, it is quite possible that the scanning will not be completed in case of interference from other environmental factors.

In order to construct a set of entire three-dimensional visualization models of peripheral nerve fascicles, the acquirement of two-dimensional images with high resolution is regarded as a basis and the most important tache. To achieve the goal of biomimetic three-dimensional reconstruction, the smaller the distance between two-dimensional images is, the better, thus, such three-dimensional reconstruction becomes more accurate, and the matching between images gets better. For this purpose, in the experiments, the selected interlayer space between two-dimensional images is 3 μm, that is to say, the voxel size is 3 μm, which can meet the requirements of three-dimensional reconstruction, however, the resulted huge picture information cannot be managed by the existing software for three-dimensional reconstruction, and the segmentation between nerve fascicles and connective tissues cannot reach the perfect segmentation by using the existing software, for this purpose we have independently developed a set of mathematical algorithms used for automatic segmentation on peripheral nerve fascicles and reconstruction of them, which are compatible with the environments generated by supercomputers, thereby achieving a goal of automatic and rapid acquisition of visualization biomimetic three-dimensional models of peripheral nerve fascicles.

Figure 5A:
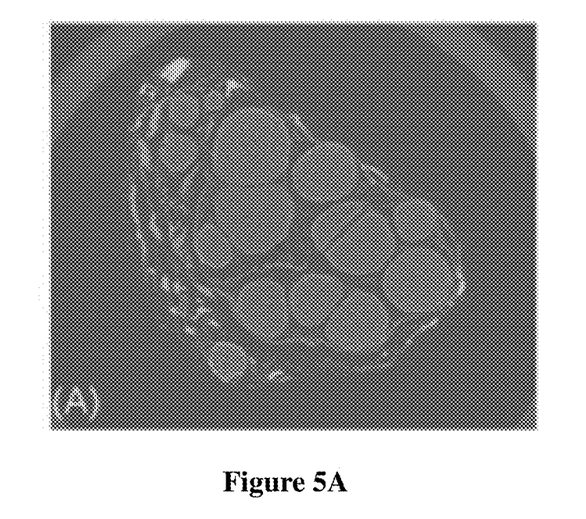
FIG. 5A shows the original image.
Figure 5B:
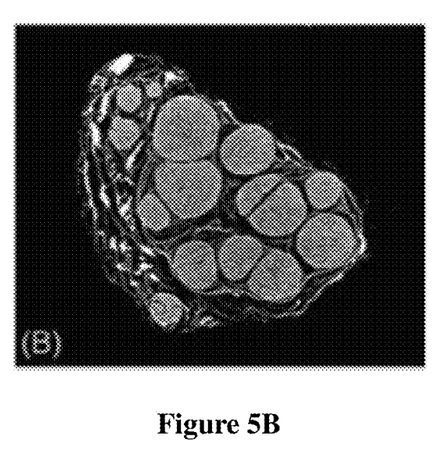
FIG. 5B shows the textural features of the extracted region of interest.
Figure 5C:
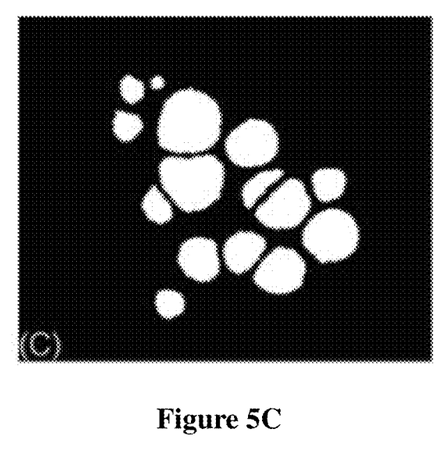
FIG. 5C shows automatically extracted profile of nerve fascicles based on textural features.
Figure 5D:
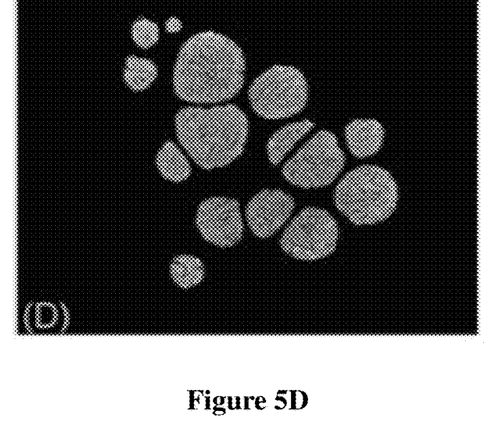
FIG. 5D shows the extracted nerve fascicles after the region of interest is merged.

FIGS. 5A-5D show the automatic segmentation process of peripheral nerve fascicles, wherein FIG. 5A is the original image; FIG. 5B indicates the textural features of the extracted region of interest; FIG. 5C refers to automatically extracted profile of nerve fascicles based on textural features; FIG. 5D refers to the extracted nerve fascicles after the region of interest is merged.

Figure 6A:
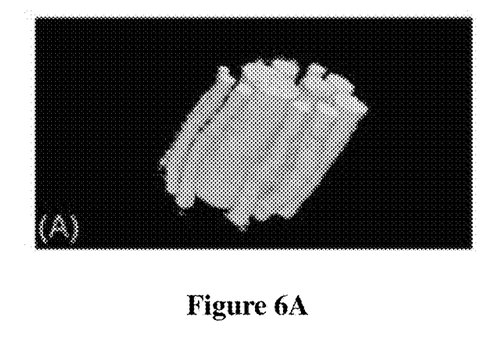
FIG. 6A shows the reconstruction performance after 1500 pictures are combined together.
Figure 6B:
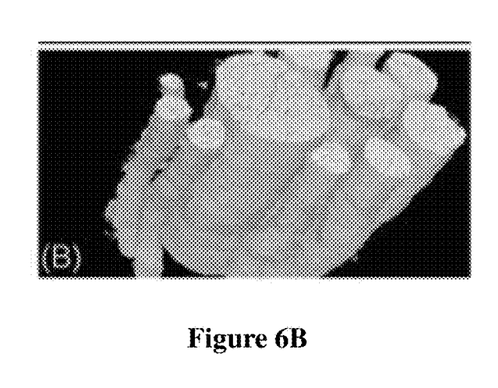
FIG. 6B shows the amplified reconstruction performance after 1500 pictures are combined together.
Figure 6C:
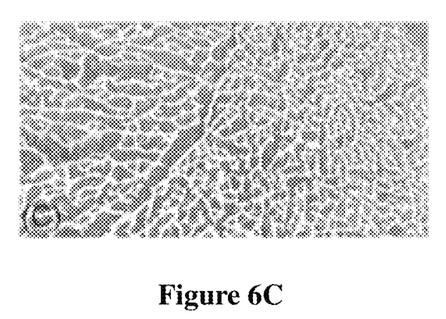
FIG. 6C shows the reconstruction performance of endoneurium.
Figure 6D:
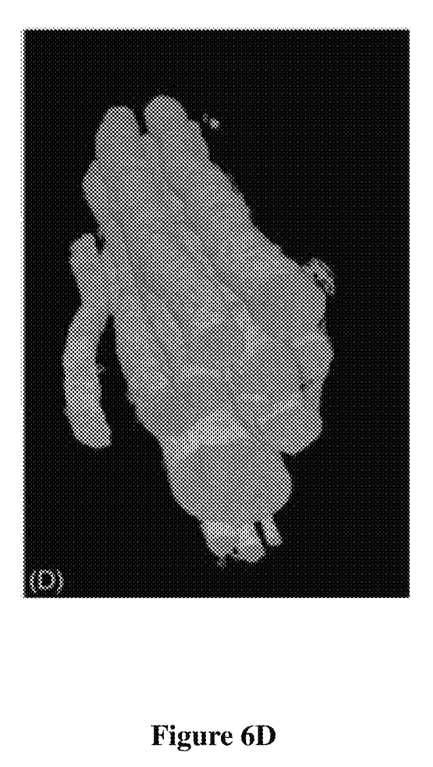
FIG. 6D shows the reconstruction performance after 7248 pictures are combined together.

FIGS. 6A-6D show views resulted from three-dimensional visualization reconstruction of peripheral nerve fascicles, wherein FIG. 6A refers to the reconstruction performance after 1500 pictures are combined together; FIG. 6B refers to the amplified reconstruction performance after 1500 pictures are combined together; FIG. 6C shows the reconstruction performance of endoneurium; FIG. 6D shows the reconstruction performance after 7248 pictures are combined together.

Under the circumstances of the preferred parameter settings, it needs a longer cycle to scan images by using Micro CT, from a dozen hours to dozens of hours, as a result, slight changes of environmental factors in the machine will influence the scanning outcome, especially moisture variation in the environment. In order to avoid the influence of moisture, peripheral nerve specimens can be placed in preservative films or preservation bags to insulate moisture during scanning, and meanwhile preservative films or preservation bags have not any adverse impact on scanning performance.

Specifically, during acquiring the segmented images of nerve fascicles, auto-adaptable topological variations are mainly utilized to acquire the profile of nerve fascicles, without a need to provide the initial profile and central point in advance, and the computation will be quickly completed by the system at the computing center.

According to an embodiment, the length of the peripheral nerve specimen is 2.1 cm, and the interlayer spacing space between two adjacent pictures is 3 μm, 3 μm*7000=2.1 cm, consequently the number of acquired pictures by scanning is 7000; DICOM (Digital Imaging and Communications in Medicine) files for so many such pictures occupy a capacity of 63 Gigabytes (G), and conventional workstations are not capable of managing such huge pictures. Supercomputers are used to accomplish the picture processing in the present invention. Performing a three-dimensional rendering will take 10 hours when using a conventional computer, while it takes only 10 min to perform a three-dimensional rendering when using a supercomputer. In the meanwhile, the constructing method of the invention can also be used in big data applications.

Furthermore, the present invention also provides a method for three-dimensional reconstruction of human peripheral nerves, which includes the above-mentioned constructing method for visualization models of human peripheral nerve fascicles.

The present invention will now be further illustrated by way of embodiments below.

Embodiment 1

Step 1: Obtaining Human Peripheral Nerves, and Performing a Corresponding Pretreatment on them.

Obtaining human peripheral nerves, removing fat and connective tissues around nerves under the microscope, followed by fixing in 4% paraformaldehyde solution for 4 days. Cutting them into small segments of about 2 cm length. At room temperature, soaking the dissected nerve tissues into 40%-50% iodine solution (aqueous solution of iodine, Lugol's iodine solution Sigma-Aldrich, St. Louis, USA) followed by oscillation treatment for 2 days, the staining is judged successful until the color changes from milky white to brown.

Wrapping the iodine preparation stained specimens of peripheral nerves with tinfoil and placing them into liquid nitrogen for quick-freezing, then taking the specimens out of liquid nitrogen and placing them in freeze-dryer for thermostatic drying at a temperature of −80° C. for 3 days to remove moisture, and putting them in the airtight and dry container to be stored for use later.

Step 2: Scanning the Pretreated Human Peripheral Nerves by Using Micro CT.

Scanning the above-mentioned peripheral nerve specimens obtained from Step 1 by using a Scanco μCT50 from Scanco Medical AG, Switzerland, and setting the scanner in accordance with the following scanning parameters:

Visual scanning field of Micro CT: 9 mm;
Energy/current intensity: 55 kVp, 72 μA, 6 W
Filtration: 0.1 mm Al
Calibration: 55 kVp, 0.1 mm Al, BH: organic glass (PMMA board)
Integration time: 1500 ms
Average data: 3
Diameter of visual field: 9 mm
Voxel size: 3 μm
Specimens: 3400
Projection/180°: 1500.

Step 3: Extracting Nerve Fascicles from the Original Image by Using Segmentation Formulas.

Drawing the gray histogram based on original two-dimensional images acquired by Micro CT scanning, obtaining the reasonable binarization threshold after computation and performing binarization processing of images. Acquiring the profile of nerve fascicles by extracting the information of textural features from binary images and differentiating between internal and external regions of nerve fascicles. Obtaining the segmented images of nerve fascicles by filtering out the information outside the profile on the binary images in view of the acquired the profile.

Step 4: Forming a Visualization Model of Nerve Fascicles Based on Three-Dimensional Reconstruction of the Segmented Two-Dimensional Images.

The method of the present invention performs volume rendering mainly by using VTK, and obtains three-dimensional visualization models of nerve fascicles by multi-node parallel computing under the Linux environment provided by a supercomputer, moreover, the method considerably shortens the duration required for volume rendering of big data.

The above descriptions are just preferred embodiments of the invention, not for the purpose of limiting the invention, and any modification, equivalent substitution or improvement within the spirit and principles of the invention, should be included in the scope of protection of the present invention.

The invention claimed is:

1. A constructing method for visualization models of human peripheral nerve fascicles, comprising the steps of:
obtaining human peripheral nerves, and treating the peripheral nerves by staining with an iodine preparation in combination with a freeze-drying method;
scanning the pretreated peripheral nerves by using Micro CT to acquire lossless two-dimensional images, and performing binarization processing of the two-dimensional images, then conducting image segmentation based on textural features to acquire images of nerve fascicles;
reconstructing the images of nerve fascicles into visualization models.

2. The constructing method according to claim 1, wherein the peripheral nerves are fixed with a fixing agent before staining with the iodine preparation, and the fixing agent is 3.5%-4.5% paraformaldehyde solution, or 9%-11% glutaraldehyde solution.

3. The constructing method according to claim 1, wherein the iodine preparation is 40%-50% iodine solution.

4. The constructing method according to claim 1, wherein the peripheral nerves are wrapped with tinfoil and placed in liquid nitrogen for freezing before the freeze-drying process.

5. The constructing method according to claim 1, wherein the diameter of visual field is set to 9 mm and the voxel size is set to 3 μm in the course of scanning the pretreated peripheral nerves by using Micro CT.

6. A method for three-dimensional reconstruction of human peripheral nerves, comprising the steps of:
obtaining human peripheral nerves, and treating the peripheral nerves by staining with an iodine preparation in combination with a freeze-drying method;
scanning the pretreated peripheral nerves by using Micro CT to acquire lossless two-dimensional images, and performing binarization processing of the two-dimensional images, then conducting image segmentation based on textural features to acquire images of nerve fascicles;
reconstructing the images of nerve fascicles into visualization models.

7. The method according to claim 6, wherein the peripheral nerves are fixed with a fixing agent before staining with the iodine preparation, and the fixing agent is 3.5%-4.5% paraformaldehyde solution, or 9%-11% glutaraldehyde solution.

8. The method according to claim 6, wherein the iodine preparation is 40%-50% iodine solution.

9. The method according to claim 6, wherein the peripheral nerves are wrapped with tinfoil and placed in liquid nitrogen for freezing before the freeze-drying process.

10. The method according to claim 6, wherein the diameter of visual field is set to 9 mm and the voxel size is set to 3 μm in the course of scanning the pretreated peripheral nerves by using Micro CT.

* * * * *